United States Patent
Hartle et al.

(10) Patent No.: US 10,913,792 B2
(45) Date of Patent: Feb. 9, 2021

(54) TREATMENT FOR RHEUMATOID ARTHRITIS

(71) Applicant: MORPHOSYS AG, Planegg (DE)

(72) Inventors: Stefan Hartle, Planegg (DE); Stephane Leclair, Planegg (DE); Amgad Shebl, Planegg (DE); Stefan Steidl, Planegg (DE); Bodo Brocks, Planegg (DE); Daniela Della Ducata, Planegg (DE); Kai Rosport, Planegg (DE)

(73) Assignee: Morphosys AG, Planegg (DE)

( * ) Notice: Subject to any disclaimer, the term of this patent is extended or adjusted under 35 U.S.C. 154(b) by 0 days.

(21) Appl. No.: 15/880,726

(22) Filed: Jan. 26, 2018

(65) Prior Publication Data

US 2018/0230208 A1  Aug. 16, 2018

Related U.S. Application Data

(63) Continuation of application No. 14/429,996, filed as application No. PCT/EP2013/069501 on Sep. 19, 2013, now abandoned.

(60) Provisional application No. 61/703,871, filed on Sep. 21, 2012.

(30) Foreign Application Priority Data

Sep. 20, 2012 (EP) .................................. 12185235

(51) Int. Cl.
| | | |
|---|---|---|
| C07K 16/24 | (2006.01) | |
| A61K 31/519 | (2006.01) | |
| A61K 39/395 | (2006.01) | |
| A61K 39/00 | (2006.01) | |

(52) U.S. Cl.
CPC .......... *C07K 16/243* (2013.01); *A61K 31/519* (2013.01); *A61K 39/3955* (2013.01); *A61K 2039/505* (2013.01); *A61K 2039/54* (2013.01); *A61K 2039/545* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,267,958 B1 | 7/2001 | Andya et al. | |
| 7,455,836 B2 | 11/2008 | Hamilton et al. | |
| 2007/0053871 A1 | 3/2007 | Li et al. | |
| 2010/0209434 A1 | 8/2010 | Bishop et al. | |
| 2011/0182905 A1* | 7/2011 | Takada ................ | C07K 16/243 424/145.1 |
| 2012/0156196 A1 | 6/2012 | Casey | |

FOREIGN PATENT DOCUMENTS

| | | |
|---|---|---|
| EP | 2142174 B1 | 12/2010 |
| EP | 2341061 A1 | 7/2011 |
| JP | 2010-241718 | 10/2010 |
| WO | WO-98/14476 A1 | 4/1998 |
| WO | WO 2006/122797 A2 | 11/2006 |
| WO | WO 2008/064321 A2 | 5/2008 |
| WO | WO 2009/038760 A2 | 3/2009 |
| WO | WO 2010/066762 A1 | 5/2009 |
| WO | WO 2009/064399 A1 | 6/2010 |
| WO | WO-2010/071923 A1 | 7/2010 |
| WO | WO-2010/071924 A1 | 7/2010 |
| WO | WO 2010/128035 A1 | 11/2010 |
| WO | WO-2011/109365 A2 | 9/2011 |
| WO | WO-2013/004806 A1 | 1/2013 |

OTHER PUBLICATIONS

Bork, A. Powers and pitfalls in sequence analysis: the 70% hurdle. Genome Res 10: 398-400. (Year: 2000).*
Bork et al. Go hunting in sequence databases but watch out for the traps. Trends in Genetics. 12(10): 425-427. (Year: 1996).*
Brenner, S.E. Errors in genome function. Trends in Genetics 15(4): 132-133, 1999. (Year: 1999).*
Brorson et al. Mutational analysis of avidity and fine specificity of anti-levan antibodies. J Immunol 163: 6694-6701, (Year: 1999).*
Brummell et al. (Biochemistry 32:1180-1187. (Year: 1993).*
Burks et al. PNAS 94:412-417. (Year: 1997).*
Colman, P.M. Research in Immunol. 145:33-36. (Year: 1994).*
Doerks et al. Protein annotation: detective work for function prediction. Trends in Genetics 14(6): 248-250. (Year: 1998).*
Jang et al. (Molec. Immunol.35:1207-1217. (Year: 1998).*
Kobayashi et al. Protein Engineering 12:879-844. (Year: 1999).*
Tokuriki et al. Stability effects of mutations and protein evolvability. Curr Opin Structural Biol 19: 596-604. (Year: 2009).*
Ngo et al. Computational complexity, protein structure prediction, and the Levinthal paradox. The Protein Folding Problem and Tertiary Structure Prediction, pp. 492-495. (Year: 1994).*
Skolnick et al. From genes to protein structure and function: novel applications of computational approaches in the genomic era. Trends in Biotech 18(1): 34-39. (Year: 2000).*
Smith et al. The challenges of genome sequence annotation or "The devil is in the details". Nature Biotech 15: 1222-1223. (Year: 1997).*
Wells. J.A. Additivity of mutational effects in proteins. Biochemistry 29 (37): 8509-8517. (Year: 1990).*
Rowe et al., Handbook of Pharmaceutical Excipients 5th edition, pp. 718-721 (Year: 2005).*
Cook et al., "Blockade of collagen-induced arthritis post-onset by antibody to granulocyte-macrophage colony-stimulated (GM-CSF): requirement for GM-CSF in the effector phase of disease," Arthritis Research, Jun. 2001, 3(5): 293-298.

(Continued)

*Primary Examiner* — Gary B Nickol
*Assistant Examiner* — Jegatheesan Seharaseyon
(74) *Attorney, Agent, or Firm* — Foley & Lardner LLP

(57) ABSTRACT

The present invention provides anti-GM-CSF antibodies for use in the treatment of rheumatoid arthritis. Anti-GM-CSF antibodies, in particular MOR103, are administered to patients suffering from rheumatoid arthritis at dosages that are beneficial in a clinical setting.

7 Claims, 4 Drawing Sheets

Specification includes a Sequence Listing.

(56) References Cited

OTHER PUBLICATIONS

Warne et al., "Development of high concentration protein biopharmaceuticals: The use of platform approaches in formulation development," Eur. J. Pharm & Biopharm., 2011, 78:208-212.
Herman, A.C., "Characeterisation, Formulation, and Stability of Neupogen® (Filgrastim), a Recombinant Human Granulocyte-Colony Stimulating Factor," Formulation Characterisation and Stability of Protein Drugs, Pearlman et al., Eds., 1996, 303-328.
Katdare et al., Eds., Excipient Development for Pharmaceutical, Biotechnology, and Drug Delivery Systems, Informa Healthcare, 2006, 296-301.
Medimmune LLC, "A Study to Evaluate the Efficacy and Safety of CAM-3001 (Drug) in Subjects With Rheumatoid Arthritis—view of NCT01050988 on May 8, 2012," Archive retrieved from: https://clinicaltrials.gov/archive/NCT01050998/2012_05_08 on Nov. 9, 2017.

\* cited by examiner

Figure 1

MOR103:

Variable Heavy Chain Peptide (CDRs are bold and underlined):

QVQLVESGGGLVQPGGSLRLSCAASGFTFSSYWMNWVRQAPGKGLEWVSGIENKYAGGATYYAASVKGRFTISRDNSKNTLYLQMNSLRAEDTAVYYCARGFGTDFWGQGTLVTVSS (SEQ ID NO.: 8)

Variable Heavy Chain DNA:

CAGGTGCAGCTGGTCGAGTCTGGCGGCGGACTGGTGCAGCCTGGCGGCAGCCTGAGACTGAGCTGTGCCGCCAGCGGCTTCACCTTCAGCAGCTACTGGATGAACTGGGTGAGGCAGGCCCCTGGCAAGGGCCTGGAGTGGGTGTCCGGCATCGAGAACAAGTATGCCGGCGGAGCCACCTACTACGCCGCCAGCGTGAAGGGCCGGTTCACCATCAGCCGGGACAACAGCAAGAACACCCTGTACCTGCAGATGAACAGCCTGAGGGCCGAGGACACCGCCGTGTACTACTGTGCCAGGGGCTTCGGCACCGATTTCTGGGGCCAGGGCACCCTGGTGACAGTCAGCTCA (SEQ ID NO.: 10)

Variable Light Chain Peptide (CDRs are bold and underlined):
DIELTQPPSVSVAPGQTARISCSGDSIGKKYAYWYQQKPGQAPVLVIYKKRPSGIPERFSGSNSGNTATLTISGTQAEDEADYYCSAWGDKGMVFGGGTKLTVLGQ (SEQ ID NO.: 9)

Variable Light Chain DNA:
GACATCGAGCTGACCCAGCCCCCCAGCGTGTCTGTGGCCCCTGGCCAGACCGCCCGGATCAGCTGCTCCGGCGACAGCATCGGCAAGAAGTACGCCTACTGGTATCAGCAGAAGCCCGGCCAGGCCCCCGTGCTGGTGATCTACAAGAAGCGGCCCAGCGGCATCCCCGAGCGGTTCAGCGGCAGCAACAGCGGCAACACCGCCACCCTGACCATCAGCGGCACCCAGGCCGAGGACGAGGCCGACTACTACTGCTCCGCCTGGGGCGACAAGGGCATGGTGTTTGGCGGCGGAACAAAGTTAACCGTGCTGGGGCAG (SEQ ID NO.: 11)

TREATMENT FOR RHEUMATOID ARTHRITIS

CROSS-REFERENCE TO RELATED APPLICATIONS

This application is a Continuation of U.S. application Ser. No. 14/429,996, which is the U.S. National Stage application of PCT/EP2013/069501, filed Sep. 19, 2013, which claims priority from U.S. Provisional Application No. 61/703,871, filed Sep. 21, 2012.

FIELD OF THE INVENTION

The present invention provides anti-GM-CSF antibodies for use in the treatment of rheumatoid arthritis, and methods for the treatment of rheumatoid arthritis using such antibodies. Anti-GM-CSF antibodies, in particular MOR103, are administered to patients suffering from rheumatoid arthritis at dosages that are beneficial in a clinical setting.

BACKGROUND OF THE INVENTION

Rheumatoid arthritis (RA) is a chronic systemic inflammatory disease that affects 0.5% to 1% of the adult population worldwide. RA primarily affects the joints and is characterized by chronic inflammation of the synovial tissue, which eventually leads to the destruction of cartilage, bone and ligaments and can cause joint deformity. RA has a peak incidence between 40 and 60 years of age and affects primarily women. The cause of RA is not known; however, certain histocompatibility antigens are associated with poorer outcomes. Nonsteroidal anti-inflammatory drugs (NSAIDs) provide only symptomatic relief. Disease-modifying antirheumatic drugs (DMARDs), the cornerstone of RA treatment throughout all stages of the disease, maintain or improve physical function and retard radiographic joint damage. Pro-inflammatory cytokines, such as tumor necrosis factor-alpha (TNFα), interleukin-1, interleukin-6 and granulocyte macrophage colony stimulating factor (GM-CSF), which lead to the activation and proliferation of immune cells, are found to be increased in the inflamed joint.

More recently, biological compounds, such as antibodies, that target tumor necrosis factor alpha (TNFα), B-cells, or T-cells have been used to treat RA, but still many patients fail to respond to these therapies. Colony-stimulating factors (CSFs) have been suggested for a potential point of intervention for inflammatory disorders, such as RA (reviewed e.g. in Nat Rev Immunol (2008) 8, 533-44) or Nat Rev Rheumatol (2009) 5, 554-9). One of such CSF is granulocyte-macrophage colony-stimulation factor (GM-CSF).

MOR103 is a fully human anti-GM-CSF antibody (Mol Immunol (2008) 46, 135-44; WO 2006/122797). MOR 103 is also in a clinical Phase Ib trial for multiple sclerosis. The present invention describes the development of a clinically efficacious treatment regimen comprising MOR103 for RA.

SUMMARY OF THE INVENTION

In one aspect, the present invention provides an anti-GM-CSF antibody for use in the treatment of a patient suffering from rheumatoid arthritis, wherein said antibody is administered to said patient in a manner to achieve a therapeutically effective antibody level in the blood of said patient equal or higher compared to the intravenous administration of said antibody at a dose of at least 1.0 mg/kg when administered weekly over at least four weeks.

In another aspect, the present invention also provides a method to treat a patient suffering from rheumatoid arthritis, said method comprising administering to said patient an anti-GM-CSF antibody in a manner to achieve a therapeutically effective antibody level in the blood of said patient equal or higher compared to the intravenous administration of said antibody at a dose of at least 1.0 mg/kg when administered weekly over at least four weeks.

In an embodiment, the anti-GM-CSF antibody is administered intravenously, optionally at a dosage of at least 1.0 mg/kg, or at a dose of about 1.0 mg/kg or about 1.5 mg/kg. In an embodiment, the anti-GM-CSD antibody is administered weekly, over at least four weeks.

In an embodiment, the anti-GM-CSF antibody is administered subcutaneously, optionally at a dose of at least 2.0 mg/kg, or at a dose of about 2.0 mg/kg, about 3.0 mg/kg or about 4.0 mg/kg. In an embodiment, the anti-GM-CSF antibody is administered biweekly, monthly or bimonthly. In another embodiment, the antibody is administered at a fixed dose of about 75 mg, of about 100 mg, of about 150 mg, of about 200 mg, of about 300 mg or of about 400 mg. Administration of fixed doses may be every week, every second week, every third week, every fourth week or every sixth week.

In an embodiment, the dosage of anti-GM-CSF antibody administered to said patient and frequency of said administration is sufficient to provide and maintain a serum concentration of said antibody at at least 2 µg/ml in said patient over the duration of said treatment.

In another aspect, the present invention provides an anti-GM-CSF antibody, wherein said anti-GM-CSF antibody is an antibody comprising an HCDR1 region of sequence GFTFSSYWMN (SEQ ID NO.: 2), an HCDR2 region of sequence GIENKYAGGATYYAASVKG (SEQ ID NO.: 3), an HCDR3 region of sequence GFGTDF (SEQ ID NO.: 4), an LCDR1 region of sequence SGDSIGKKYAY (SEQ ID NO.: 5), an LCDR2 region of sequence KKRPS (SEQ ID NO.: 6), and an LCDR3 region of sequence SAWGDKGM (SEQ ID NO.: 7) for use in the treatment of a patient suffering from rheumatoid arthritis, wherein said antibody is administered to said patient in a manner to achieve a therapeutically effective antibody level in the blood of said patient equal or higher compared to the intravenous administration of said antibody at a dose of at least 1.0 mg/kg when administered weekly over at least four weeks.

In another aspect, the present invention provides an anti-GM-CSF antibody, wherein said anti-GM-CSF antibody is an antibody comprising an HCDR1 region of sequence GFTFSSYWMN (SEQ ID NO.: 2), an HCDR2 region of sequence GIENKYAGGATYYAASVKG (SEQ ID NO.: 3), an HCDR3 region of sequence GFGTDF (SEQ ID NO.: 4), an LCDR1 region of sequence SGDSIGKKYAY (SEQ ID NO.: 5), an LCDR2 region of sequence KKRPS (SEQ ID NO.: 6), and an LCDR3 region of sequence SAWGDKGM (SEQ ID NO.: 7) for use in the treatment of a patient suffering from rheumatoid arthritis, wherein said antibody is administered intravenously at a dose of about 1.0 mg/kg or at a dose of about 1.5 mg/kg and wherein said antibody in administered weekly over at least four weeks.

In another aspect, the present invention provides an anti-GM-CSF antibody for use in the treatment of a patient suffering from rheumatoid arthritis, wherein said antibody is administered to said patient in a manner to achieve a therapeutically effective antibody level in the blood of said patient equal or higher compared to the intravenous administration of said antibody at a dose of at least 1.0 mg/kg or at least 1.5 mg/kg when administered weekly over at least four weeks, and wherein said anti-GM-CSF antibody is administered in combination with a DMARD, such as methotrexate.

In an embodiment, the administration of said antibody to achieve such a therapeutically effective amount comprises the administration of said antibody intravenously at a dose at least 0.6, at least 0.7, at least 0.8, at least 0.9 or at least 1.0 mg/kg. In other embodiments, the antibody of the present invention is administered intravenously at a dose of about 1.0 mg/kg or a dose of about 1.5 mg/kg. Administration may be monthly, biweekly (every two weeks) or weekly.

In another aspect, the present invention provides an anti-GM-CSF antibody for use in the treatment of a patient suffering from rheumatoid arthritis, wherein said antibody is administered to said patient subcutaneously in a manner to achieve a therapeutically effective antibody level in the blood of said patient equal or higher compared to the intravenous administration of said antibody at a dose of at least 1.0 mg/kg or at least 1.5 mg/kg when administered weekly over at least four weeks, and wherein said anti-GM-CSF antibody is administered in combination with a DMARD, such as methotrexate.

In an embodiment, the administration of said antibody to achieve such a therapeutically effective amount comprises the administration of said antibody subcutaneously at a dose of at least 1.0, at least 1.5, at least 2.0, at least 2.5, at least 3.0, at least 3.5 or at least 4.0 mg/kg. In other embodiments, the antibody of the present invention is administered subcutaneously at a dose of about 2.0 mg/kg, a dose of about 3.0 mg/kg or a dose of about 4.0 mg/kg. Administration may be monthly, biweekly (every two weeks) or weekly.

In an embodiment, the administration of said antibody to achieve such a therapeutically effective amount comprises the administration of said antibody subcutaneously at a fixed dose of about 40 mg, at a fixed dose of 75 mg, at a fixed dose of 100 mg, at a fixed dose of 140 mg, at a fixed dose of 150 mg, at a fixed dose of 180 mg, at a fixed dose of 200 mg, at a fixed dose of 280 mg, at a fixed dose of 300 mg or at a fixed dose of 400 mg. Administration of fixed doses may be every week, every second week, every third week, every fourth week or every sixth week.

In another aspect, the present invention provides a method of treating a patient suffering from rheumatoid arthritis, said method comprising administering to said patient an anti-GM-CSF antibody subcutaneously at (i) a dose of at least 1.0 mg/kg, or
(ii) a fixed dose of between 40 mg and 400 mg.

The anti-GM-CSF antibody may be administered to said patient in a manner to achieve to a serum concentration of said antibody at at least 2 μg/ml in said patient over the duration of said treatment. The antibody may be administered to said patient in a manner to achieve a therapeutically effective antibody level in the blood of said patient equal or higher compared to the intravenous administration of said antibody at a dose of at least 1.0 mg/kg when administered weekly over at least four weeks.

In another aspect, the present invention provides an anti-GM-CSF antibody for inhibiting progression of structural joint damage in a rheumatoid arthritis patient comprising administering to said patient said antibody in a manner to achieve a therapeutically effective antibody level in the blood of said patient equal or higher compared to the intravenous administration of said antibody at a dose of at least 1.0 mg/kg when administered weekly over at least four weeks.

BRIEF DESCRIPTION OF THE DRAWINGS

FIG. 1 shows the amino acid sequence and the DNA sequence of MOR04357.

DESCRIPTION

Figure 2:
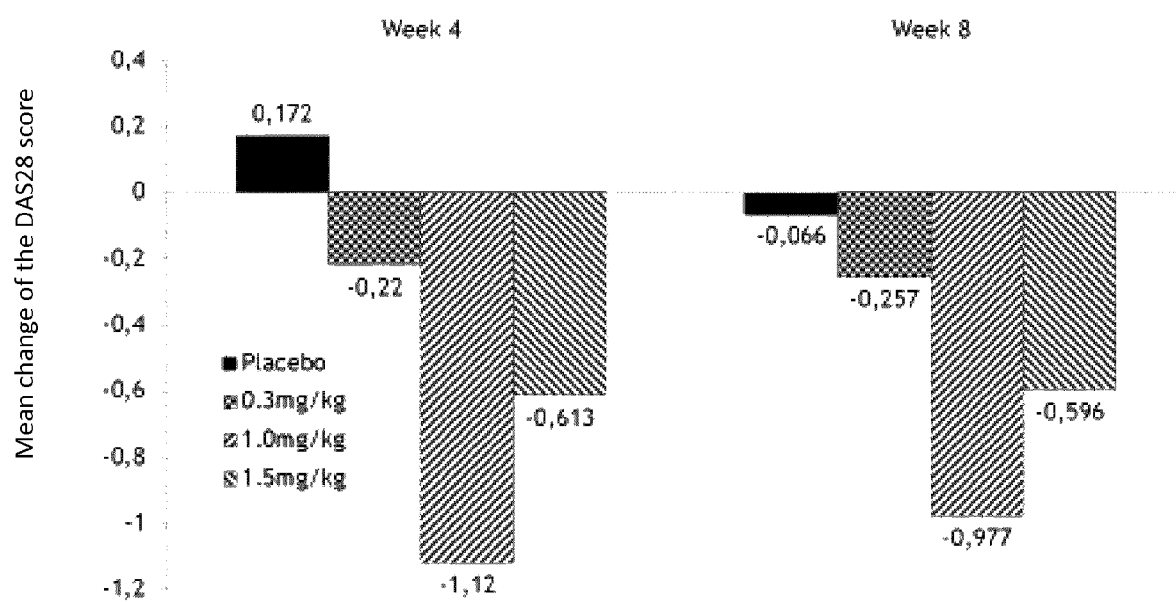
FIG. 2 shows the mean changes of the DAS28 score after four weeks (left panel) and after eight weeks (right panel) of treatment compared. DAS28 score changes are compared to baseline levels, i.e. disease status prior to treatment.

The terms "GM-CSF" and "GMCSF" refer to the protein known as GM-CSF or Granulocyte-macrophage colony-stimulating factor, having the following synonyms: Colony-stimulating factor 2, CSF2, GMCSF, GM-CSF, Granulocyte-macrophage colony-stimulating factor, MGC131935, MGC138897, Molgramostin, Sargramostim. Human GM-CSF has the amino acid sequence of (UniProt P04141):

(SEQ ID NO.: 1)
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE

"MOR103" is an anti-GM-CSF antibody whose amino acid sequence and DNA sequence is provided in FIG. 1. "MOR103" and "MOR04357" and "MOR4357" are used as synonyms to describe the antibody shown in FIG. 1. MOR04357 comprises an HCDR1 region of sequence GFTFSSYWMN (SEQ ID NO.: 2), an HCDR2 region of sequence GIENKYAGGATYYAASVKG (SEQ ID NO.: 3), an HCDR3 region of sequence GFGTDF (SEQ ID NO.: 4), an LCDR1 region of sequence SGDSIGKKYAY (SEQ ID NO.: 5), an LCDR2 region of sequence KKRPS (SEQ ID NO.: 6), and an LCDR3 region of sequence SAWGDKGM (SEQ ID NO.: 7). MOR04357 comprises a variable heavy chain of the sequence QVQLVESGGGLVQPGGSLRLS-CAASGFTFSSYWMNWVRQAPGKGLEWVSGIENKY-AGGA TYYAASVKGRFTISRDNSKNTLYLQMNSL-RAEDTAVYYCARGFGTDFWGQGTLVTVSS (SEQ ID NO.: 8) and a variable light chain of the sequence DIELTQPPSVSVAPGQ-TARISCSGDSIGKKYAYWYQQKPGQAPVLVIYKKRPS-GIPERFSGS NSGNTATLTISGTQAEDEADYYC-SAWGDKGMVFGGGTKLTVLGQ (SEQ ID NO.: 9).

In certain embodiments, the antibody used in the present invention is an antibody specific for GM-CSF. In other embodiments, the antibody used in the present invention is an antibody specific for a polypeptide encoding an amino acid sequence comprising SEQ ID NO.: 1.

As used herein, "specifically for" or "specifically binding to" refers to an antibody selectively or preferentially binding to GM-CSF. Preferably the binding affinity for antigen is of Kd value of $10^{-9}$ mol/l or lower (e.g. $10^{-10}$ mol/l), preferably with a Kd value of $10^{-10}$ mol/l or lower (e.g. $10^{-12}$ mol/l). The binding affinity is determined with a standard binding assay, such as surface plasmon resonance technique (BIA-CORE®).

In certain embodiments, the antibody used in the present invention is MOR103. In other embodiments, the antibody used in the present invention is an antibody comprising an HCDR1 region of sequence GFTFSSYWMN (SEQ ID NO.: 2), an HCDR2 region of sequence GIENKYAG-GATYYAASVKG (SEQ ID NO.: 3), an HCDR3 region of sequence GFGTDF (SEQ ID NO.: 4), an LCDR1 region of sequence SGDSIGKKYAY (SEQ ID NO.: 5), an LCDR2 region of sequence KKRPS (SEQ ID NO.: 6), and an LCDR3 region of sequence SAWGDKGM (SEQ ID NO.: 7). In other embodiments, the antibody used in the present invention is an antibody comprising a variable heavy chain of the sequence QVQLVESGGGLVQPGGSLRLS-CAASGFTFSSYWMNWVRQAPGKGLEWVSGIENKY-AGGA TYYAASVKGRFTISRDNSKNTLYLQMNSL-RAEDTAVYYCARGFGTDFWGQGTLVTVSS (SEQ ID NO.: 8) and a variable light chain of the sequence DIELTQPPSVSVAPGQ-TARISCSGDSIGKKYAYWYQQKPGQAPVLVIYKKRPS-GIPERFSGS NSGNTATLTISGTQAEDEADYYC-SAWGDKGMVFGGGTKLTVLGQ (SEQ ID NO.: 9). In other embodiments, the antibody used in the present invention is an antibody which cross-competes with an antibody comprising an HCDR1 region of sequence GFTFSSYWMN (SEQ ID NO.: 2), an HCDR2 region of sequence GIEN-KYAGGATYYAASVKG (SEQ ID NO.: 3), an HCDR3 region of sequence GFGTDF (SEQ ID NO.: 4), an LCDR1 region of sequence SGDSIGKKYAY (SEQ ID NO.: 5), an LCDR2 region of sequence KKRPS (SEQ ID NO.: 6), and an LCDR3 region of sequence SAWGDKGM (SEQ ID NO.: 7). In other embodiments, the antibody used in the present invention is an antibody which binds to the same epitope like an antibody specific for GM-CSF comprising an HCDR1 region of sequence GFTFSSYWMN (SEQ ID NO.: 2), an HCDR2 region of sequence GIENKYAGGATYYAASVKG (SEQ ID NO.: 3), an HCDR3 region of sequence GFGTDF (SEQ ID NO.: 4), an LCDR1 region of sequence SGDSIGKKYAY (SEQ ID NO.: 5), an LCDR2 region of sequence KKRPS (SEQ ID NO.: 6), and an LCDR3 region of sequence SAWGDKGM (SEQ ID NO.: 7).

The term "antibody" is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" herein comprise a portion of an intact antibody which retains the ability to bind antigen. Examples of antibody fragments include Fab, Fab', F(ab')2, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin.

A "human antibody" herein is one comprising an amino acid sequence structure that corresponds with the amino acid sequence structure of an antibody obtainable from a human B-cell, and includes antigen-binding fragments of human antibodies. Such antibodies can be identified or made by a variety of techniques, including, but not limited to: production by transgenic animals (e.g., mice) that are capable, upon immunization, of producing human antibodies in the absence of endogenous immunoglobulin; selection from phage display libraries expressing human antibodies or human antibody; generation via in vitro activated B; and isolation from human antibody producing hybridomas.

In certain embodiments, the antibody used in the present invention is a monoclonal antibody.

In other embodiments, the antibody used in the present invention is a chimeric, a humanized or a human antibody. In preferred embodiments, the antibody used in the present invention is a human antibody.

In certain embodiments, the antibody used in the present invention is administered in combination with an additional drug that treats RA.

The additional drug may be one or more medicaments, and include, for example, immunosuppressive agents, non-steroidal anti-inflammatory drugs (NSAIDs), disease modifying anti-rheumatic drugs (DMARDs) such as methotrexate (MTX), anti-B-cell surface marker antibodies, such as anti-CD20 antibodies (e.g. rituximab), TNF-alpha-inhibitors, corticosteroids, and co-stimulatory modifiers, or any combination thereof. Optionally, the second or additional drug is selected from the group consisting of non-biological DMARDs, NSAIDS, and corticosteroids.

These additional drugs are generally used in the same dosages and with administration routes as used hereinbefore and hereinafter. If such additional drugs are used at all, preferably, they are used in lower amounts than if the first medicament were not present, especially in subsequent dosings beyond the initial dosing with the first medicament, so as to eliminate or reduce side effects caused thereby. The combined administration of an additional drug includes co-administration (concurrent administration), using separate formulations or a single pharmaceutical formulation, and consecutive administration in either order, wherein preferably there is a time period while both (or all) active agents (medicaments) simultaneously exert their biological activities.

The term "DMARD" refers to "Disease-Modifying Anti-Rheumatic Drugs" and includes among others hydroxycloroquine, sulfasalazine, methotrexate, leflunomide, azathioprine, D-penicillamine, gold salts (oral), gold salts (intramuscular), minocycline, cyclosporine including cyclosporine A and topical cyclosporine, and TNF-inhibitors, including salts, variants, and derivatives thereof. Exemplary DMARDs herein are non-biological, i.e. classic, DMARDs, including, azathioprine, chloroquine, hydroxychloroquine, leflunomide, methotrexate and sulfasalazine.

Methotrexate is an especially preferred DMARD of the present invention. Therefore, in certain embodiments, the antibody used in the present invention is administered in combination with a DMARD. In other embodiments, the antibody used in the present invention is administered in combination with methotrexate.

A "TNF-inhibitor" as used herein refers to an agent that inhibits, to some extent, a biological function of TNF-alpha, generally through binding to TNF-alpha and/or its receptor and neutralizing its activity. Examples of TNF inhibitors include etanercept (ENBREL®), infliximab (REMICADE®), adalimumab (HUMIRA®), certolizumab pegol (CIMZIA®), and golimumab (SIMPONI®).

"Treatment" of a patient or a subject refers to both therapeutic treatment and prophylactic or preventative measures. The terms "effective amount" or "therapeutically effective" refer to an amount of the antibody that is effective for treating rheumatoid arthritis. Such effective amount can result in any one or more of reducing the signs or symptoms of RA (e.g. achieving ACR20), reducing disease activity (e.g. Disease Activity Score, DAS20), slowing the progression of structural joint damage or improving physical function. In one embodiment, such clinical response is comparable to that achieved with intravenously administered anti-GM-CSF antibody.

The antibody of the present invention may be administered in different suitable forms. Potential forms of administration include systemic administration (subcutaneous, intravenous, intramuscular), oral administration, inhalation, transdermal administration, topical application (such as topical cream or ointment, etc.) or by other methods known in the art. The doses (in mg/kg) specified in the present invention refer to milligrams of antibody per kilogram of body weight of the patient. In vitro cell based assays showed that an anti-GM-CSF antibody (MOR103) is capable of inhibiting several GM-CSF mediated responses. Evaluated responses include TF-1 cell proliferation, STAT5 phosphorylation, polymorphonuclear neutrophils (PMN) migration, PMN up-regulation of CD11b, monocyte up-regulation of MHC II, and eosinophil survival. Complete inhibitory effects were generally reached at concentrations of about 0.2 µg/ml anti-GM-CSF antibody. GM-CSF concentrations up to 1 ng/ml were applied in such studies. As a reference, GM-CSF levels in the synovial fluid of RA patients were reported to be <500 pg/ml. It is reasonable to consider that similar GM-CSF concentrations as used in these in vitro studies are present in affected tissues of RA patients To effectively treat RA it may be important for an anti-GM-CSF antibody to penetrate the synovium. There is evidence to suggest that monoclonal antibodies can distribute into the synovium when dosed subcutaneously or intravenously. Based on a predicted penetration rate of 30%, continuous GM-CSF production and considering patient heterogeneity, the minimal or sub-optimal clinical effect level in RA patients is anticipated to be at a serum concentration of approximately 2 µg/ml antibody (thus, approximately 10-fold higher than the inhibitory concentration derived from in vitro studies).

A specific anti-GM-CSF antibody (MOR103) has been administered to patients with active rheumatoid arthritis who received 4 intravenous weekly doses of 0.3, 1, and 1.5 mg/kg. The anti-GM-CSF antibody showed significant clinical efficacy on DAS28, EULAR, ACR20, ACR50, ACR70 and tender joint counts following once a week dosing with 1 and 1.5 mg/kg as compared to placebo.

In certain embodiments, the antibody of the present invention is administered intravenously. In other embodiments, the antibody of the present invention is administered subcutaneously.

From other therapeutic antibodies it is known that a concentration that leads to a certain level of the antibody in the blood when administered intravenously corresponds to about 50-76% of the blood concentration achieved when the same antibody concentration is administered subcutaneously (Meibohm, B.: Pharmacokinetics and Pharmacodynamics of Biotech Drugs, Wiley-VCH, 2006). For MOR103 this ratio was determined to be 52%, i.e. a given concentration administered subcutaneously leads to a blood concentration which is equivalent to about 52% of the blood concentration when the same given concentration is administered intravenously. Therefore, the concentration of a subcutaneous formulation needs to be about twice as high to achieve the same drug blood level as compared to an intravenous formulation.

In certain embodiments the blood level to be achieved in a patient is equal or higher compared to the blood concentration achieved with intravenous administration of the antibody of the present invention at a dose of at least 1.0 mg/kg when administered weekly over at least four weeks.

In alternative embodiments said blood concentration to be achieved is equal or higher compared to the blood concentration achieved with intravenous administration of the antibody of the present invention at a doses of at least 0.4, 0.5, 0.6, 0.7, 0.8 or 0.9 mg/kg when administered weekly over at least four weeks. In alternative embodiments the blood level to be achieved in a patient is equal or higher compared to the blood concentration achieved with intravenous administration of the antibody of the present invention at a dose of at least 1.0 mg/kg when administered weekly over at least two weeks or at least three weeks. In alternative embodiments the blood level to be achieved in a patient is equal or higher compared to the blood concentration achieved with intravenous administration of the antibody of the present invention at a dose of at least 1.0 mg/kg when administered biweekly over at least two weeks or at least four weeks.

In certain embodiments, the antibody of the present invention is administered intravenously. In other embodiments, the antibody of the present invention is administered intravenously at a dose at least 0.6, at least 0.7, at least 0.8, at least 0.9 or at least 1.0 mg/kg. In other embodiments, the antibody of the present invention is administered intravenously at a dose of about 1.0 mg/kg or a dose of about 1.5 mg/kg.

In certain embodiments, the antibody of the present invention is administered subcutaneously. Various dosing regimen have been simulated using the subcutaneous delivery of MOR103 in order to produce plasma concentrations that are similar those obtained after 1 mg/kg iv, a dose that was efficacious in RA. The majority of simulations produce trough concentration values greater than 2 ug/mL, a value that is believed to be the minimum blood concentration that is required to produce efficacy in the context of an anti-GM-CSF antibody. These studies indicate that subcutaneous doses of 1, 2, 3 and 4 mg/kg can produce plasma concentration similar to 1 mg/kg, IV depending on the dosing frequency.

In other embodiments, the antibody of the present invention is administered subcutaneously at a dose at least 1.0, at least 1.5, at least 2.0, at least 2.5, at least 3.0, at least 3.5 or at least 4.0 mg/kg. In other embodiments, the antibody of the present invention is administered subcutaneously at a dose of about 2.0 mg/kg, a dose of about 3.0 mg/kg or a dose of about 4.0 mg/kg. In certain embodiments, the antibody of the present invention is subcutaneously administered biweekly, monthly or bimonthly.

In other embodiments, the antibody of the present invention is administered subcutaneously at a fixed dose. In such "fixed dose" treatment the antibody is administered at a certain, fixed, concentration, i.e. without taking into account a patient's body weight. In certain embodiments, the antibody of the present invention is administered at a fixed dose of between 40 mg and 400 mg, optionally at a fixed dose of 75 mg, at a fixed dose of 100 mg, at a fixed dose of 140 mg, at a fixed dose of 150 mg, at a fixed dose of 180 mg, at a fixed dose of 200 mg, at a fixed dose of 280 mg, at a fixed dose of 300 mg or at a fixed dose of 400 mg. Administration of fixed doses may be every week, every second week, every third week, every fourth week or every sixth week. Typically, the antibody will be administered weekly at a fixed dose.

In an embodiment, the antibody will be administered weekly, at a fixed subcutaneous dose of 40, 56, 70, 75 100, 140, 150, 180, 200, 210, or 280 mg.

In an embodiment, the antibody will be administered biweekly, at a fixed subcutaneous dose of 70, 75, 100, 140, 150, 180, 200, 210, 280 or 300 mg.

In an embodiment, the antibody will be administered monthly, at a fixed subcutaneous dose of 100, 140, 150, 180, 200, 210, 280, 300, 320, 350. 360 or 400 mg.

In an embodiment, the antibody is administered in a dose sufficient to maintain trough concentration of antibody of at least 2 ug/mL. The trough concentration of antibody may be maintained at 2.0 ug/mL, 2.5 ug/mL, 3.0 ug/mL, 3.5 ug/mL, 4.0 ug/mL, 4.5 ug/mL or 5.0 ug/mL, during the course of therapy.

In alternative embodiments, the antibody will be administered weekly, at a fixed subcutaneous dose of 28 or 35 mg, In certain embodiments, the present invention provides an anti-GM-CSF antibody for use in the treatment of a patient suffering from rheumatoid arthritis, wherein said antibody is administered to said patient in a manner to achieve a therapeutically effective antibody level in the blood of said patient equal or higher compared to the intravenous administration of said antibody at a dose of at least 1.0 mg/kg when administered weekly over at least four weeks.

In certain embodiments, the present invention provides a method to treat a patient suffering from rheumatoid arthritis, said method comprising administering to said patient an anti-GM-CSF antibody in a manner to achieve a therapeutically effective antibody level in the blood of said patient equal or higher compared to the intravenous administration of said antibody at a dose of at least 1.0 mg/kg when administered weekly over at least four weeks.

In certain embodiments, the present invention provides an anti-GM-CSF antibody for inhibiting progression of structural joint damage in a rheumatoid arthritis patient comprising administering to said patient said antibody in a manner to achieve a therapeutically effective antibody level in the blood of said patient equal or higher compared to the intravenous administration of said antibody at a dose of at least 1.0 mg/kg when administered weekly over at least four weeks.

The terms "drug" and "medicament" refer to an active drug to treat rheumatoid arthritis or joint damage or symptoms or side effects associated with RA. The term "pharmaceutical formulation" refers to a preparation which is in such form as to permit the biological activity of the active ingredient or ingredients, i.e. the antibody of the present invention, to be effective, and which contains no additional components which are unacceptably toxic to a subject to which the formulation would be administered. Such formulations are sterile.

The antibody herein is preferably recombinantly produced in a host cell transformed with nucleic acid sequences encoding its heavy and light chains (e.g. where the host cell has been transformed by one or more vectors with the nucleic acid therein). The preferred host cell is a mammalian cell, most preferably a PER.C6 cell.

Therapeutic formulations of the antibody of the present invention are prepared for storage by mixing the antibody having the desired degree of purity with optional pharmaceutically acceptable carriers, excipients or stabilizers in the form of lyophilized formulations or aqueous solutions. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes {e.g. Zn-protein complexes); and/or non-ionic surfactants such as TWEEN™ (such as Tween-80), PLURONICS™ or polyethylene glycol (PEG).

In certain embodiments, the present invention provides a pharmaceutical composition comprising an antibody of the present invention and a pharmaceutically acceptable carrier and/or excipient for use in any of the methods provided in the present invention. In certain embodiments, the formulation for the antibody of the present invention consists of 30 mM histidine, pH 6.0, 200 mM sorbitol and 0.02% Tween-80. In other embodiments, the formulation for the antibody of the present invention consists of PBS, pH 6.2 (0.2 g/l KCl, 0.96 g/l $KH_2PO_4$, 0.66 g/l $Na_2HPO_4 \times 7H_2O$, 8 g/l NaCl).

EXAMPLES

Example 1: Design and Concept of a Clinical Phase Ib/Phase IIa Trial

A multi-center, randomized, double-blinded, placebo-controlled study to evaluate the safety, preliminary clinical activity and immunogenicity of multiple doses of MOR103 administered intravenously to patients with active rheumatoid arthritis was conducted.

Primary outcome measures were the adverse event rate and the safety profile. Secondary outcome measures included DAS28 scores, ACR scores and EULAR28 response criteria.

The clinical trial comprised three treatment arms. In each treatment arm patient received either placebo or MOR103. The MOR103 doses were 0.3 mg/kg body weight for treatment arm 1, 1.0 mg/kg body weight for treatment arm 2 and 1.5 mg/kg body weight for treatment arm 3. MOR103 and placebo were administered intravenously, weekly with 4 doses in total.

Summary of the Treatment Arms:

| Arms | Assigned Interventions |
| --- | --- |
| Experimental: Group 1: MOR103, experimental Biological: MOR103 0.3 mg/kg or placebo | Drug: MOR103 MOR103 0.3 mg/kg or placebo iv x 4 doses |
| Experimental: Group 2: MOR103, experimental Biological: MOR103 1.0 mg/kg or placebo | Drug: MOR103 MOR103 1.0 mg/kg or placebo iv x 4 doses |
| Experimental: Group 3: MOR103, experimental Biological: MOR103 1.5 mg/kg or placebo | Drug: MOR103 MOR103 1.5 mg/kg or placebo iv x 4 doses |

Eligible for participation in the study were patients of 18 years and older and of either sex (male and female). Healthy volunteers were not accepted.

Inclusion criteria were as follows:
Rheumatoid arthritis (RA) per revised 1987 ACR criteria
Active RA: ≥3 swollen and 3 tender joints with at least 1 swollen joint in the hand, excluding the PIP joints
CRP>5.0 mg/L (RF and anti-CCP seronegative); CRP>2 mg/l (RF and/or anti-CCP seropositive)
DAS28≤5.1
Stable regimen of concomitant RA therapy (NSAIDs, steroids, non-biological DMARDs).
Negative PPD tuberculin skin test
Exclusion criteria were as follows:
Previous therapy with B or T cell depleting agents other than Rituximab (e.g. Campath). Prior treatment with Rituximab, TNF-inhibitors, other biologics (e.g. anti-IL-1 therapy) and systemic immunosuppressive agents is allowed with a washout period.
Any history of ongoing, significant or recurring infections
Any active inflammatory diseases other than RA
Treatment with a systemic investigational drug within 6 months prior to screening
Women of childbearing potential, unless receiving stable doses of methotrexate or leflunomide
Significant cardiac or pulmonary disease (including methotrexate-associated lung toxicity)
Hepatic or renal insufficiency

Example 2: Patient Recruitment and Patient Population

Clinical sites for patient recruitment, screening and treatment were located in Bulgaria, Germany, the Netherlands, Poland and the Ukraine.

96 patients were included in the trial. 27 patients received placebo, 24 patients received MOR103 at a dose of 0.3 mg/kg, 22 patients received MOR103 at a dose of 1.0 mg/kg and 23 patients received MOR103 at a dose of 1.5 mg/kg. The average age and the average Body Mass Index (BMI) was about the same for all treatment groups. Key characteristics are summarized in the following Table:

| | | MOR 103 Active Treatment Groups | | | |
| --- | --- | --- | --- | --- | --- |
| Characteristic | Placebo N = 27 | 0.3 mg/kg N = 24 | 1.0 mg/kg N = 22 | 1.5 mg/kg N = 23 | Total active N = 69 |
| Age | 53.8 | 57.4 | 49 | 53 | 53.3 |
| BMI | 26.3 | 26.3 | 26.1 | 25.7 | 26.0 |
| Gender-Female | 19 (70%) | 21 (88%) | 17 (77%) | 18 (78%) | 56 (81%) |
| White | 27 | 24 | 22 | 23 | 69 |

90% of all patients of the study were previously treated with DMARDs. The most commonly used DMARD was methotrexate (75% of all patients). The rate of previous treatment with DMARDs was comparable in all treatment arms.

Prior to administration of MOR103 or the placebo the disease activity of all patients was measured according to accepted guidelines by calculating the DAS28 score, a 28-joint Disease Activity Score (see e.g. Ann Rheum Dis (2009) 68, 954-60). DAS28 score is a validated and commonly used tool to quantify the disease status of RA patients. The average DAS28 score was comparable for all treatment arms.

Example 3: Safety Profile

Based on the available observed safety data, MOR103 showed a favorable safety profile among all doses tested. The key observations are as follows:
No deaths were observed during the conduct of the trial
No infusion related reactions were observed
Two serious adverse events (SAEs) were observed:
One patient in the placebo group developed paronychia
One patient in the 0.3 mg/kg treatment arm developed pleurisy
More treatment-emergent adverse effects (TEAEs) were observed in the placebo group (25.9%) than in the active groups (14.5%)
Most TEAEs were mild
No severe TEAEs were observed in the active groups
In summary, it can be concluded that treatment with MOR103 at all doses tested is safe. Two serious adverse events were observed, both none in the treatment arms that showed clinical efficacy (see below). Sub-cutaneous administration of MOR103 at a dose that leads to an antibody drug level in the blood of patients equivalent to the intravenous application of the present study is expected to show a similar safety profile.

Example 4: Efficacy—DAS28

4 weeks and 8 weeks after the first administration of MOR103 (or placebo) the DAS28 scores of all patients was determined. A decrease in DAS28 scores correlates to diminished disease severity. Results are shown in FIG. 2 as the mean changes compared to baseline, i.e. disease status prior to treatment.

The placebo group only shows marginal changes. Patients treated with MOR103 at 0.3 mg/kg showed a slight decrease in DAS28 scores, indicating slightly less severity of the disease. In contrast, patients treated with MOR103 at 1.0 mg/kg or with 1.5 mg/kg showed a significant decrease in DAS28 scores, indicating the high efficacy of MOR103 at these doses.

Example 5: Efficacy—ACR20

Figure 3:
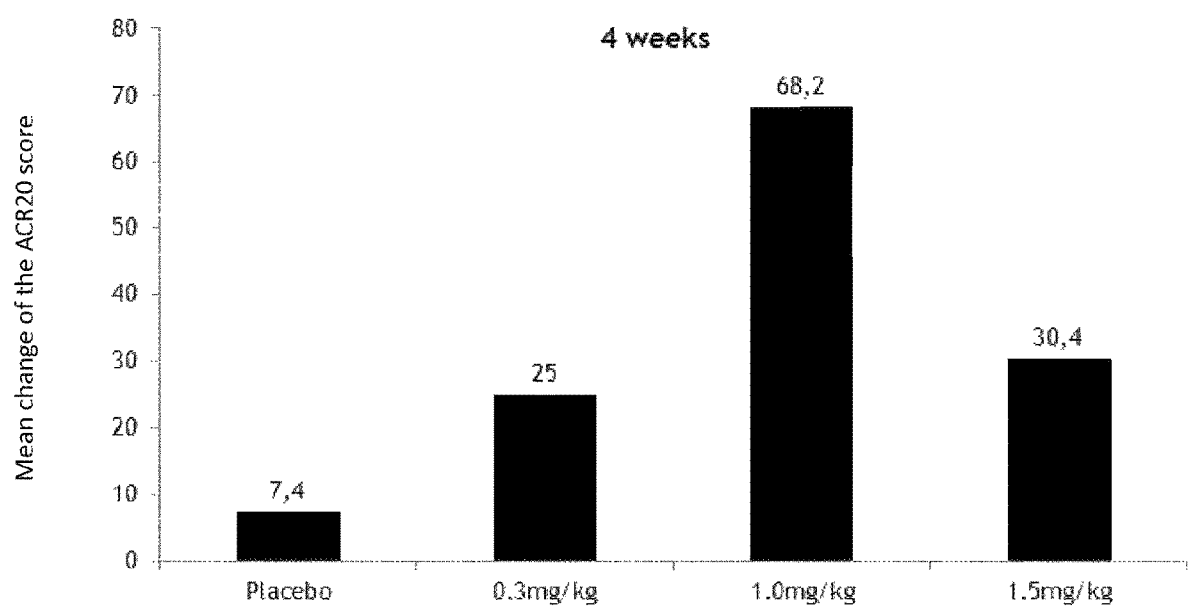
FIG. 3 shows the average ACR20 score of all treatment arms after four weeks. An increase of the ACR20 scores corresponds to an improvement of the severity of disease.
Figure 4:
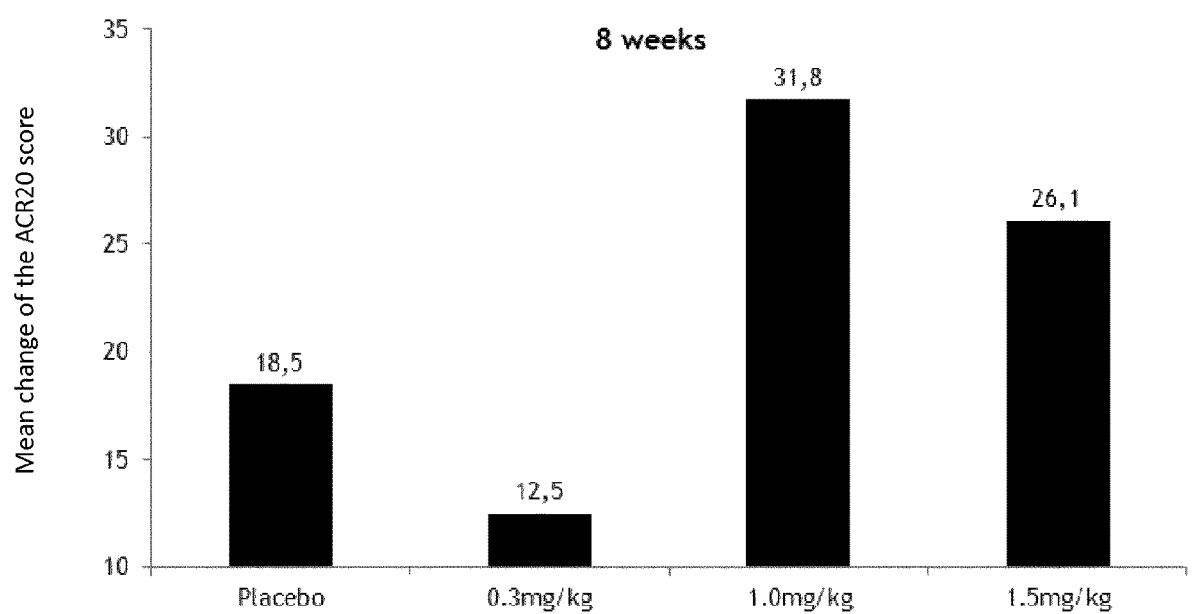
FIG. 4 shows the average ACR20 score of all treatment arms after eight weeks. An increase of the ACR20 scores corresponds to an improvement of the severity of disease.

As another measure of efficacy the ACR20 criteria were used. ACR criteria measure improvement in tender or swollen joint counts and improvement in certain other parameters. The procedure to measure ACR scores is highly standardized. The present clinical trial applied the respective applicable guidelines. Results are depicted in FIGS. 3 and 4. A higher score corresponds to an improvement in the severity of the disease.

In line with the results of the DAS28 scores (see Example 4), also the ACR scores show a strong clinical improvement of patients' condition upon treatment with either 1.0 mg/kg MOR103 or 1.5 mg/kg MOR103. The improvement after 4 weeks is highly significant for the 1.0 mg/kg group ($p<0.0001$). Taken together, the ACR20 scores confirm the surprising finding that the efficacy of MOR103 can already be shown with a comparably low number or patients in each treatment arm and a comparably short treatment period.

Example 6: Clinical Trial with Additional Doses of MOR103

The clinical trial set out herein above is repeated with additional doses of MOR103. MOR103 is administered to patients intravenously at a dose of 0.5 mg/kg (treatment arm 1) and 0.75 mg/kg (treatment arm 2). All other parameters are identical to Example 1.

Both treatment arms show a favorable safety profile and demonstrate clinical efficacy as measured by DAS28 scores and ACR20 scores.

Example 7: Clinical Trial with a Sub-Cutaneous Formulation of MOR103

The clinical trial set out herein above is repeated with a sub-cutaneous formulation of MOR103. In order to achieve similar levels of MOR103 in the blood of patients as observed for intravenous treatment, the sub-cutaneous dose of MOR103 is increased.

In different treatment arms MOR103 is administered to patients at 1.5 mg/kg, 2.0 mg/kg, 3.0 mg/kg and 4.0 mg/kg. The drug is administered sub-cutaneously, either biweekly, monthly or bimonthly. All other parameters are identical to Example 1.

All treatment arms show a favorable safety profile and demonstrate clinical efficacy as measured by DAS28 scores and ACR20 scores.

Example 8: Clinical Trial with a Sub-Cutaneous Formulation of MOR103 at a Fixed Dose Example 7 is repeated with a fixed dose of MOR103. In different treatment arms MOR103 is administered to patients at fixed dose of 75 mg, of 100 mg, of 150 mg, of 200 mg, of 300 mg and of 400 mg. The drug is administered sub-cutaneously every week, every second week, every fourth week or every sixth week. All other parameters are identical to the Examples described herein above.

All treatment arms show a favorable safety profile and demonstrate clinical efficacy as measured by DAS28 scores and ACR20 scores.

The invention claimed is:

1. A method of treating a patient suffering from rheumatoid arthritis, said method comprising administering to said patient a once a week anti-Granulocyte-Macrophage Colony Stimulating Factor (anti-GM-CSF) pharmaceutical composition comprising:

(a) 1-4 mg/Kg of anti-GM-CSF antibody;

(b) 30 mM histidine;

(c) 200 mM sorbitol; and (d) 0.02% Tween-80, wherein said anti-GM-CSF antibody comprises the HCDR1 region of sequence GFTFSSYWMN (SEQ ID NO.: 2), the HCDR2 region of sequence GIENKYAGGATYYAASVKG (SEQ ID NO.: 3), the HCDR3 region of sequence GFGTDF (SEQ ID NO.: 4), the LCDR1 region of sequence SGDSIGKKYAY (SEQ ID NO.: 5), the LCDR2 region of sequence KKRPS (SEQ ID NO.: 6), and the LCDR3 region of sequence SAWGDKGM (SEQ ID NO.: 7).

2. The method according to claim 1, wherein the anti-GM-CSF antibody comprises the variable heavy chain peptide of sequence:

(SEQ ID NO: 8)
QVQLVESGGGLVQPGGSLRLSCAASGFTFSSYWMNWVRQAPGKGLEWVSG

IENKYAGGATYYAASVKGRFTISRDNSKNTLYLQMNSLRAEDTAVYYCAR

GFGTDFWGQGTLVTVSS and the variable light chain peptide of sequence:

(SEQ ID NO: 9)
DIELTQPPSVSVAPGQTARISCSGDSIGKKYAYWYQQKPGQAPVLVIYKK

RPSGIPERFSGSNSGNTATLTISGTQAEDEADYYCSAWGDKGMVFGGGTK

LTVLGQ.

3. The method according to claim 1, wherein the patient is administered a dose of 1 mg/kg, 1.5 mg/kg, 2.0 mg/kg, 2.5 mg/kg, 3.0 mg/kg, 3.5 mg/kg, or 4.0 mg/kg of the anti-GM-CSF antibody.

4. The method according to claim 1, wherein the patient is administered a dose of 40 mg to 400 mg of the anti-GM-CSF antibody.

5. The method according to claim 1, wherein the patient is administered a dose of 75 mg, 100 mg, 150 mg, 180 mg, 200 mg, 300 mg, or 400 mg of the anti-GM-CSF antibody.

6. The method according to claim 1, wherein the patient is administered a dose of 150 mg of the anti-GM-CSF antibody.

7. The method according to claim 1, wherein the pharmaceutical composition is administered subcutaneously.

* * * * *

SEQUENCE LISTING

```
<160> NUMBER OF SEQ ID NOS: 9

<210> SEQ ID NO 1
<211> LENGTH: 144
<212> TYPE: PRT
<213> ORGANISM: Homo Sapiens

<400> SEQUENCE: 1

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
```

<210> SEQ ID NO 2
<211> LENGTH: 10
<212> TYPE: PRT
<213> ORGANISM: Artificial Sequence
<220> FEATURE:
<223> OTHER INFORMATION: polypeptide

<400> SEQUENCE: 2

Gly Phe Thr Phe Ser Ser Tyr Trp Met Asn
1               5                   10

<210> SEQ ID NO 3
<211> LENGTH: 19
<212> TYPE: PRT
<213> ORGANISM: Artificial Sequence
<220> FEATURE:
<223> OTHER INFORMATION: polypeptide

<400> SEQUENCE: 3

Gly Ile Glu Asn Lys Tyr Ala Gly Gly Ala Thr Tyr Tyr Ala Ala Ser
1               5                   10                  15

Val Lys Gly

<210> SEQ ID NO 4
<211> LENGTH: 6
<212> TYPE: PRT
<213> ORGANISM: Artificial Sequence
<220> FEATURE:
<223> OTHER INFORMATION: polypeptide

<400> SEQUENCE: 4

Gly Phe Gly Thr Asp Phe
1               5

<210> SEQ ID NO 5
<211> LENGTH: 11
<212> TYPE: PRT
<213> ORGANISM: Artificial Sequence
<220> FEATURE:
<223> OTHER INFORMATION: polypeptide

<400> SEQUENCE: 5

Ser Gly Asp Ser Ile Gly Lys Lys Tyr Ala Tyr
1               5                   10

<210> SEQ ID NO 6
<211> LENGTH: 5
<212> TYPE: PRT
<213> ORGANISM: Artificial Sequence
<220> FEATURE:
<223> OTHER INFORMATION: polypeptide

<400> SEQUENCE: 6

Lys Lys Arg Pro Ser
1               5

<210> SEQ ID NO 7
<211> LENGTH: 8
<212> TYPE: PRT
<213> ORGANISM: Artificial Sequence
<220> FEATURE:
<223> OTHER INFORMATION: polypeptide

<400> SEQUENCE: 7

```
Ser Ala Trp Gly Asp Lys Gly Met
1               5
```

<210> SEQ ID NO 8
<211> LENGTH: 117
<212> TYPE: PRT
<213> ORGANISM: Artificial Sequence
<220> FEATURE:
<223> OTHER INFORMATION: polypeptide

<400> SEQUENCE: 8

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Glu Asn Lys Tyr Ala Gly Gly Ala Thr Tyr Tyr Ala Ala
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
        115
```

<210> SEQ ID NO 9
<211> LENGTH: 106
<212> TYPE: PRT
<213> ORGANISM: Artificial Sequence
<220> FEATURE:
<223> OTHER INFORMATION: polypeptide

<400> SEQUENCE: 9

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Asp Lys Gly Met Val Phe Gly
                85                  90                  95

Gly Gly Thr Lys Leu Thr Val Leu Gly Gln
            100                 105
```